(12) United States Patent
Lunsford et al.

(10) Patent No.: US 6,752,756 B2
(45) Date of Patent: *Jun. 22, 2004

(54) COMBINED VESSEL DISSECTION AND TRANSECTION DEVICE AND METHOD

(75) Inventors: John P. Lunsford, San Carlos, CA (US); Charles J. Adam, San Jose, CA (US); John W. Davis, Mountain View, CA (US); Albert K. Chin, Palo Alto, CA (US)

(73) Assignee: Origin Medsystems, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/218,475

(22) Filed: Aug. 12, 2002

(65) Prior Publication Data

US 2003/0032861 A1 Feb. 13, 2003

Related U.S. Application Data

(63) Continuation of application No. 09/490,552, filed on Jan. 25, 2000, now Pat. No. 6,432,044, which is a continuation of application No. 09/227,393, filed on Jan. 8, 1999, now abandoned, which is a continuation-in-part of application No. 09/102,723, filed on Jun. 22, 1998, now Pat. No. 5,895,353.

(51) Int. Cl.[7] .............................................. A61B 17/32
(52) U.S. Cl. ....................................... 600/129; 600/127
(58) Field of Search ................................ 600/127, 128, 600/129, 130, 104, 114

(56) References Cited

U.S. PATENT DOCUMENTS

| | | |
|---|---|---|
| 79,015 A | 6/1868 | Schulz |
| 1,727,495 A | 9/1929 | Wappler |
| 2,162,681 A | 6/1939 | Ryan |
| 2,220,720 A | 11/1940 | Jett |

(List continued on next page.)

FOREIGN PATENT DOCUMENTS

| | | |
|---|---|---|
| EP | 0 681 811 A2 | 11/1995 |
| EP | 0 761 171 A2 | 3/1997 |
| WO | WO 97-26831 | 1/1997 |

*Primary Examiner*—Cary E. O'Connor
*Assistant Examiner*—Candice C. Melson
(74) *Attorney, Agent, or Firm*—Fenwick & West LLP

(57) ABSTRACT

A retractor and a surgical tool are positioned within a cannula, and a dissection cradle of the retractor is positioned at the distal end of the cannula. The retractor includes a first portion with an axis approximately parallel to the axis of the cannula and a second portion with an axis skewed relative to the axis of the cannula. The dissection cradle is located at the distal end of the second portion of the retractor, and may include two substantially parallel, spaced legs with the retractor shaped in a loop between and in a plane skewed relative to the axes of the legs, and with the loop directed away from the surgical tool. Thus, in operation, when the surgeon locates a vessel and side branch of interest, the surgeon extends the retractor to cradle the vessel in the dissection cradle. Once cradled, the retractor may be fully extended to urge the vessel away from the axis of the cannula to isolate the side branch for exposure to the surgical tool. Removable, transparent tips are selectively positioned at the distal end of the cannula for performing dissection and transection via a single cannula. Additionally, the tips are configured to align the apices of the tips with the central axis of the endoscope to maximize the visual field through the tips via the endoscope. Wing-like protrusions on an alternate tip for the cannula facilitate tissue dissection in forming a tunnel in tissue along a target vessel. Swept back forward edges on the wing-like protrusions promote easy tissue dissection using reduced force to advance the cannula and alternate tip through tissue surrounding the target vessel.

18 Claims, 16 Drawing Sheets

U.S. PATENT DOCUMENTS

| | | |
|---|---|---|
| 2,227,727 A | 1/1941 | Leggiadro |
| 2,821,190 A | 1/1958 | Chase |
| 3,313,294 A | 4/1967 | Uddenberg |
| 3,357,433 A | 12/1967 | Fourestier et al. |
| 3,835,841 A | 9/1974 | Terada |
| 3,857,386 A | 12/1974 | Ashbell |
| 3,866,601 A | 2/1975 | Russell |
| 4,190,042 A | 2/1980 | Sinnreich |
| 4,232,660 A | 11/1980 | Coles |
| 4,428,746 A | 1/1984 | Mendez |
| 4,557,255 A | 12/1985 | Goodman |
| 4,651,733 A | 3/1987 | Mobin-Uddin |
| 4,667,655 A | 5/1987 | Ogiu et al. |
| 4,744,363 A | 5/1988 | Hasson |
| 4,773,394 A | 9/1988 | Reichstein et al. |
| 4,838,246 A | 6/1989 | Hahn et al. |
| 4,858,595 A | 8/1989 | Buess et al. |
| 4,874,375 A | 10/1989 | Ellison |
| 4,991,565 A | 2/1991 | Takahashi et al. |
| 5,230,621 A | 7/1993 | Jacoby |
| 5,251,613 A | 10/1993 | Adair |
| 5,271,385 A | 12/1993 | Bailey |
| 5,275,608 A | 1/1994 | Forman et al. |
| 5,284,128 A | 2/1994 | Hart |
| 5,337,736 A | 8/1994 | Reddy |
| 5,339,803 A | 8/1994 | Mayzels et al. |
| 5,345,927 A | 9/1994 | Bonutti |
| 5,370,109 A | 12/1994 | Cuny |
| 5,374,277 A | 12/1994 | Hassler |
| 5,395,383 A | 3/1995 | Adams et al. |
| 5,419,309 A | 5/1995 | Biehl |
| 5,450,842 A | 9/1995 | Tovey et al. |
| 5,501,654 A | 3/1996 | Failla et al. |
| 5,505,686 A | 4/1996 | Willis et al. |
| 5,512,037 A | 4/1996 | Russell et al. |
| 5,535,759 A | 7/1996 | Wilk |
| 5,554,101 A | 9/1996 | Matula et al. |
| 5,558,620 A | 9/1996 | Heckele et al. |
| 5,564,615 A | 10/1996 | Bishop et al. |
| 5,569,183 A | 10/1996 | Kieturakis |
| 5,588,581 A | 12/1996 | Conlon et al. |
| 5,626,587 A | 5/1997 | Bishop et al. |
| 5,630,787 A | 5/1997 | Yabe et al. |
| 5,634,584 A | 6/1997 | Okorocha et al. |
| 5,656,012 A | 8/1997 | Sienkiewicz |
| 5,662,662 A | 9/1997 | Bishop et al. |
| 5,673,840 A | 10/1997 | Schulze et al. |
| 5,680,982 A | 10/1997 | Schulze et al. |
| 5,685,820 A | 11/1997 | Riek et al. |
| 5,690,606 A | 11/1997 | Slotman |
| 5,702,408 A | 12/1997 | Wales et al. |
| 5,704,534 A | 1/1998 | Huitema et al. |
| 5,713,505 A | 2/1998 | Huitema |
| 5,716,352 A | 2/1998 | Viola et al. |
| 5,722,934 A | 3/1998 | Knight et al. |
| 5,738,628 A | 4/1998 | Sierocuk et al. |
| 5,762,606 A | 6/1998 | Minnich |
| 5,843,121 A | 12/1998 | Yoon |
| 5,857,961 A | 1/1999 | Vanden Hoek et al. |
| 5,895,352 A | 4/1999 | Kleiner |
| 5,895,353 A | 4/1999 | Lunsford et al. |
| 5,897,487 A | 4/1999 | Ouchi |
| 5,938,620 A | 8/1999 | Daxer |
| 5,957,936 A | 9/1999 | Yoon et al. |
| 6,162,173 A | 12/2000 | Chin et al. |
| 6,176,825 B1 | 1/2001 | Chin et al. |
| 6,387,043 B1 * | 5/2002 | Yoon .......................... 600/109 |
| 6,520,975 B2 | 2/2003 | Branco |

* cited by examiner

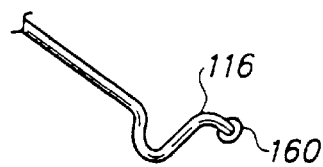
FIG. 9F
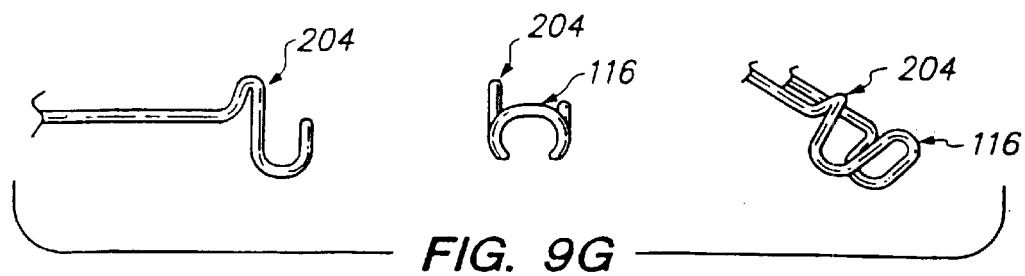
FIG. 9G
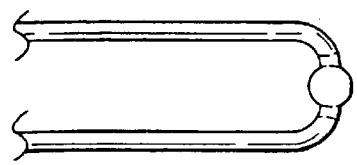 
FIG. 10A          FIG. 10B
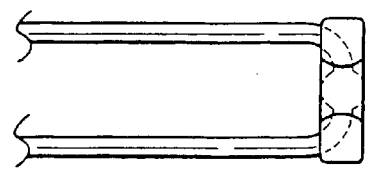 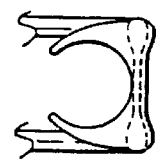
FIG. 10C          FIG. 10D

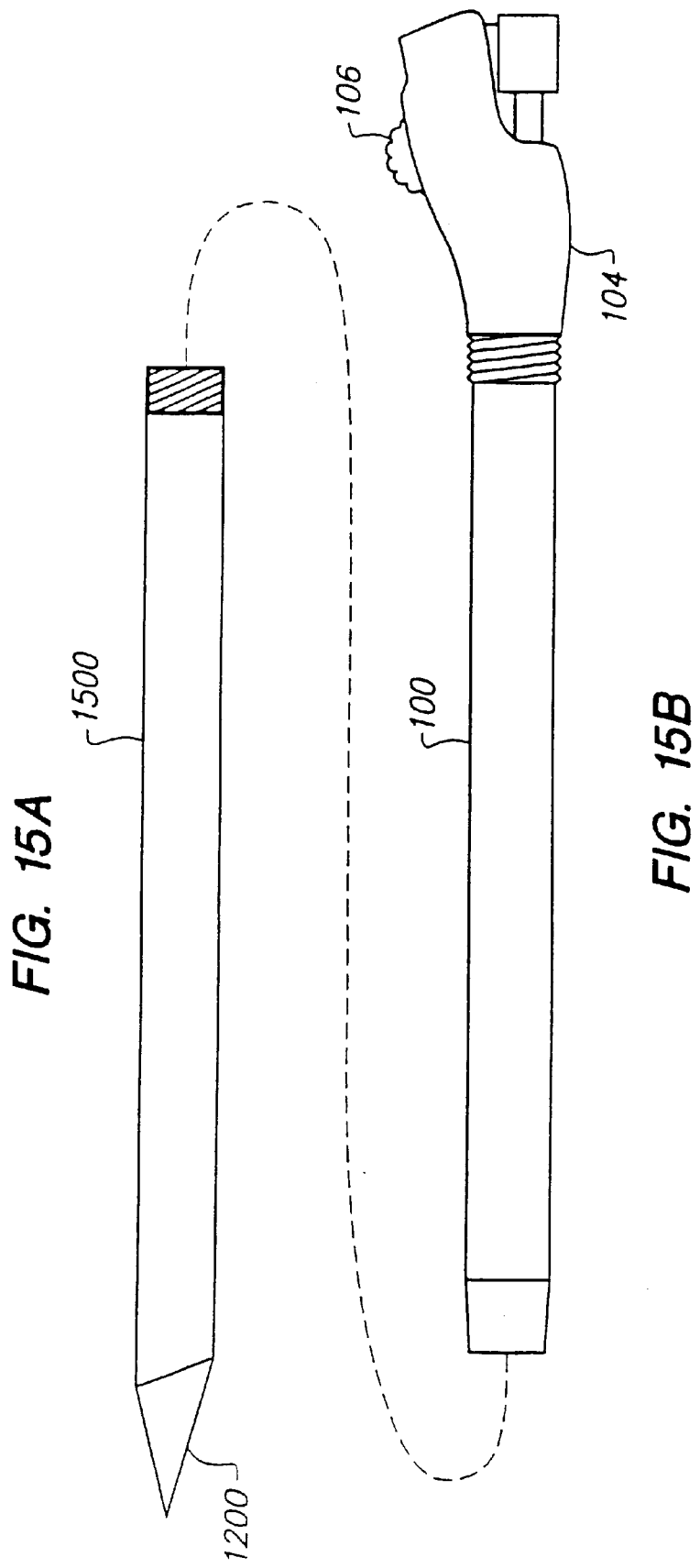

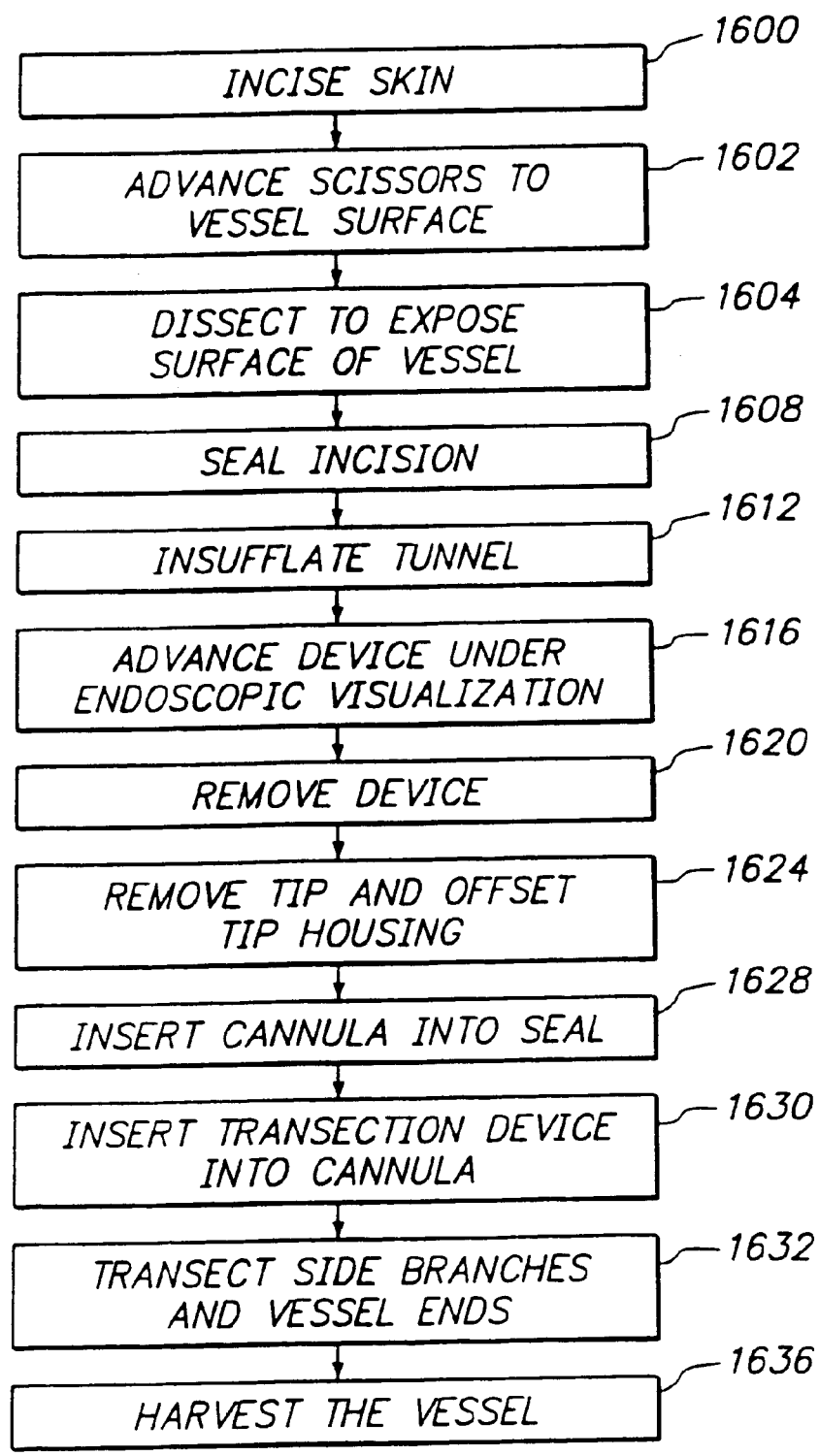

ND TRANSECTION DEVICE AND METHOD

COMBINED VESSEL DISSECTION AND TRANSECTION DEVICE AND METHOD

CROSS-REFERENCE TO RELATED APPLICATION(S)

The present application is a continuation of pending application Ser. No. 09/490,552, filed on Jan. 25, 2000, and now issued as U.S. Pat. No. 6,432,044, which is a continuation of Ser. No. 09/227,393, filed Jan. 8, 1999, now abandoned, which is a continuation-in-part application of application Ser. No. 09/102,723 filed on Jun. 22, 1998, now issued as U.S. Pat. No. 5,895,353 and the subject matter hereof is related to the subject matter of application Ser. No. 08/593,533 entitled "TISSUE SEPARATION CANNULA" filed on Jan. 24, 1996 by Albert K. Chin, now abandoned, which is a continuation-in-part application of application Ser. No. 08/502,494, entitled "TISSUE SEPARATION CANNULA AND METHOD," filed on Jul. 13, 1995, now abandoned, which prior applications are assigned to the same assignee as the present application.

FIELD OF THE INVENTION

This invention relates to a cannula used for vessel retraction, and more particularly to a cannula and method for performing both vessel dissection and transection.

BACKGROUND OF THE INVENTION

One important component of a surgical cannula is the tip, disposed on the distal end of the cannula. A properly configured tip can provide important functionality to a cannula. For example, the functions of vessel dissection and transection are commonly performed by two separate instruments. The device described in the pending application Ser. No. 08/907,691, entitled "Tissue Separation Cannula with Dissection Probe and Method," filed on Aug. 8, 1997, discloses a device for separating surrounding connective tissue from a vessel (dissection). The device described in the pending application Ser. No. 09/102,723, entitled Vessel Isolating Retractor Cannula and Method," filed on Jun. 22, 1998, discloses a device for retracting the vessel, ligating side branches, and transecting the branches to allow removal of the vessel. It is desirable to use a single device for performing the above functions.

The construction of a cannula tip also affects the visual field provided to a surgeon through an endoscope. When an endoscope is situated in a lumen of the cannula, the surgeon looks through the endoscope and through the transparent tip to view the surgical site. It is desirable to have a tip which maximizes the visual field of the endoscope.

The cannula tip may also be used to dilate a tunnel or anatomical space through tissue planes. In pending application Ser. No. 09/133,136, entitled "TISSUE DISSECTOR APPARATUS AND METHOD," filed Aug. 12, 1998, assigned to the same assignee as the present application, and which is hereby incorporated by reference, a cannula is constructed with a bulbous element near the tip of the cannula for performing tissue dilation as the cannula is advanced. Cannula tips for dilating tunnels through tissue require force in order to advance the cannula and dilate the tissue. It is desirable to have a tip which can perform tissue dilation or dissection using a minimal amount of force and causing minimal trauma.

SUMMARY OF THE INVENTION

In accordance with the present invention, a tissue retractor is positioned within a cannula with a dissection cradle end of the retractor positioned at the distal end of the cannula. The retractor includes a first portion that has an axis approximately parallel to a central axis of the cannula, and a second portion that has an axis which is at an angle with respect to the central axis of the cannula. The dissection cradle is located at the distal end of the second portion of the retractor. In another embodiment, the retractor includes two legs having substantially parallel axes that selectively protrude from the distal end of the cannula. The protruding legs support the dissection cradle formed in the shape of a loop that is positioned in a plane skewed relative to the axes of the legs, with a bottom of the loop directed away from the cannula. Thus, in operation, when the surgeon locates a vein and side branch of interest, the surgeon extends the retractor to cradle the vein in the dissection cradle. Once cradled, the retractor may be fully extended to urge the vein away from the axis of the cannula, causing the side branch to be isolated and exposed to a surgical tool. The surgical tool may then be extended from within the cannula to operate on the isolated and exposed side branch.

In another embodiment, the top of the loop of the dissection cradle is flat and thin, allowing atraumatic support of the vein, and minimizing contact between the retractor and the surgical tool. In yet a further embodiment, the retractor includes a single leg with the loop formed by the one leg of the retractor, and with a stopper coupled to the distal end of the retractor. In still another embodiment, the cannula comprises a sliding tube which encases the retractor, and in a first position is extended out to encase the second portion of the retractor, and in a second position is extended to encase only the first portion of the retractor. In response to the sliding tube being in the first position, the second and first portions of the retractor are both approximately parallel to the axis of the cannula. In response to the sliding tube being in the second position, the second portion of the retractor is skewed relative to the axis of the cannula.

In accordance with an alternate embodiment of the present invention, a removable, transparent tip is positioned at the distal end of the cannula to provide a single cannula for performing dissection and transection. When attached, the tip seals the distal end of the cannula in a fluid resistant manner. The tip is conical and ends in a sharp interior point and a slightly rounded exterior point which allows the surgeon to bluntly dissect tissue in the area of interest under endoscopic visualization. When tissue dissection is complete, the surgeon can remove the tip from the cannula, and the surgeon is now able to use the cannula to transect side branches and vessel ends. In order to maximize the visual field provided by the endoscope, the tip is configured to allow the apex of the tip to be aligned with the central axis of the endoscope. In one embodiment, a distal end of the tip is tilted in an oblique fashion to allow the apex of the tip to align with or near to the central axis of the endoscope. In an alternate embodiment, the conical end of the tip has unequal taper angles relative to a plane of transition between the cylindrical and conical portions of the tip, thus skewing the position of the apex of the tip into alignment with or near to the central axis of the endoscope.

In another embodiment, wing-like protrusions are provided about the cannula near the tip to dilate tissue surrounding the vessel of interest. In one embodiment, the wing-like protrusions are diametrically aligned in a planar configuration with tapered forward edges extending rearward from near the apex of the tip. The planar configuration of the wing-like dilating protrusions near the tip substantially reduces the resistive force encountered during advancement of the cannula through tissue. The wing-like protrusions are positioned on opposite sides of the tip to dissect tissue to form a cavity that may attain a round cross-section under insufflation, thus providing the same resultant tissue dilation as provided by a solid oval dilator, but with less force required to accomplish the tissue dilation. In an alternate embodiment, the leading edges of the wing-like protrusions are curved in a parabolic configuration away from the distal end of the cannula to provide the necessary dilation.

BRIEF DESCRIPTION OF THE DRAWINGS

FIG. 7b is a side view of the retractor 112 of FIG. 7a.

FIG. 9f illustrates multiple views of a fifth alternate embodiment of cradle 116.

FIG. 9g illustrates multiple views of an embodiment of cradle 116 having a spur.

FIG. 10a illustrates a top view of an embodiment of the cradle 116 of FIG. 9c without a "C" ring.

FIG. 10b illustrates a side view of the cradle 116 of FIG. 10a.

FIG. 10c illustrates a top view of the cradle 116 of FIG. 9c with the "C" ring attached.

FIG. 10d illustrates a side view of the cradle 116 of FIG. 10c.

FIG. 15a illustrates a side view of an alternate embodiment of offset tip 1200.

FIG. 15b illustrates a side view of a cannula 100 modified for use with the offset tip 1200 of FIG. 15a.

FIG. 16 is a flow chart illustrating a method of dissecting and transecting vessels according to the present invention.

FIG. 17b illustrates a side view of the embodiment of offset tip dilator 1716 of FIG. 17a.

DETAILED DESCRIPTION OF THE PREFERRED EMBODIMENTS

Figure 1:
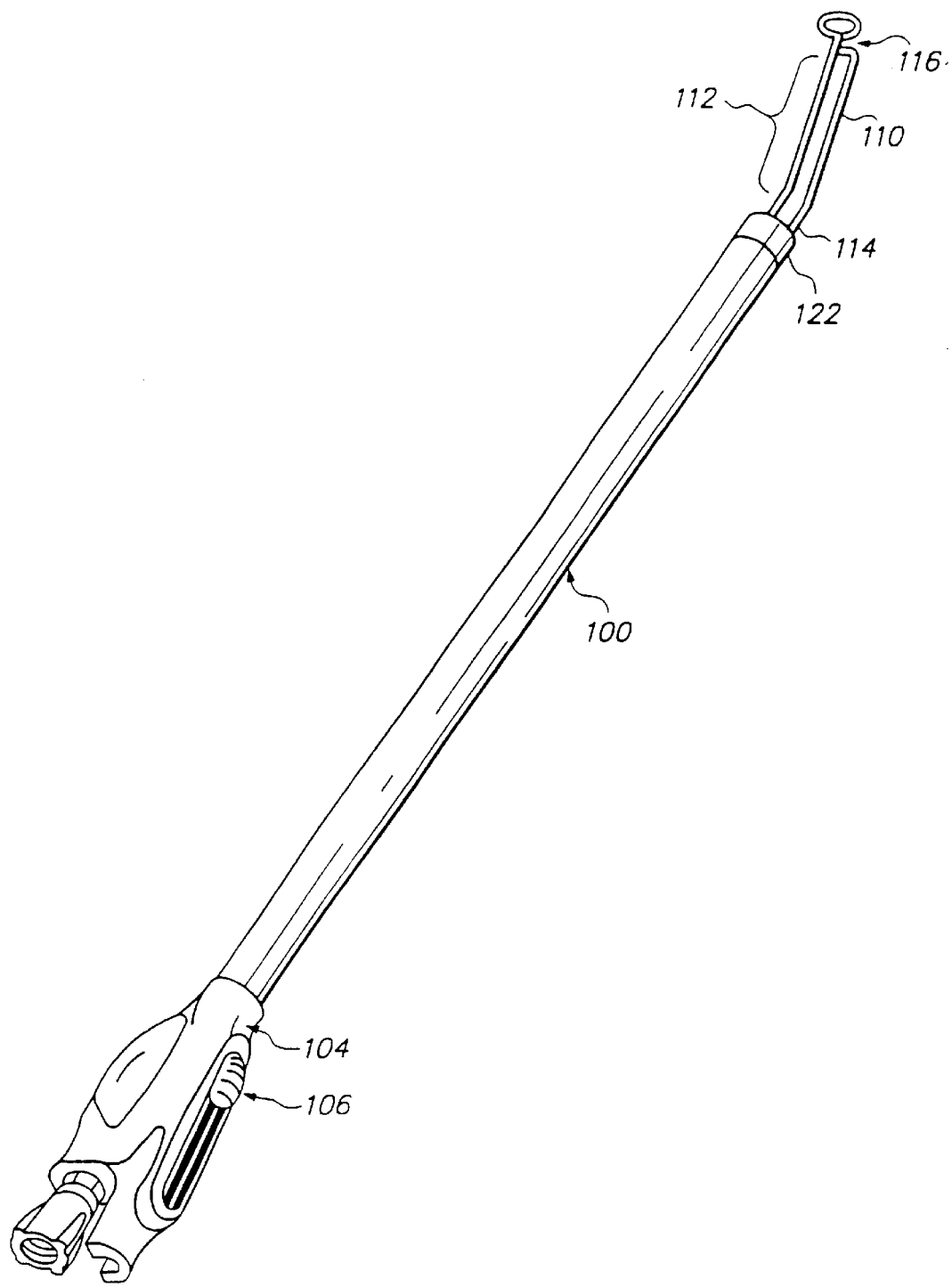
FIG. 1 is a perspective view of a preferred embodiment of cannula 100 showing retractor 112 in an extended position.

FIG. 1 illustrates a perspective view of a preferred embodiment of cannula 100 showing retractor 112 in an extended position. Cannula 100 includes an outer housing 102 of bioinert material such as polymed UD that may be approximately 12" to 18" in length. The proximal end of the cannula 100 is disposed in handle 104 that includes a button 106 which is coupled to retractor 112 for controlling the translational movement of retractor 112, as described in more detail below.

Figure 2A:
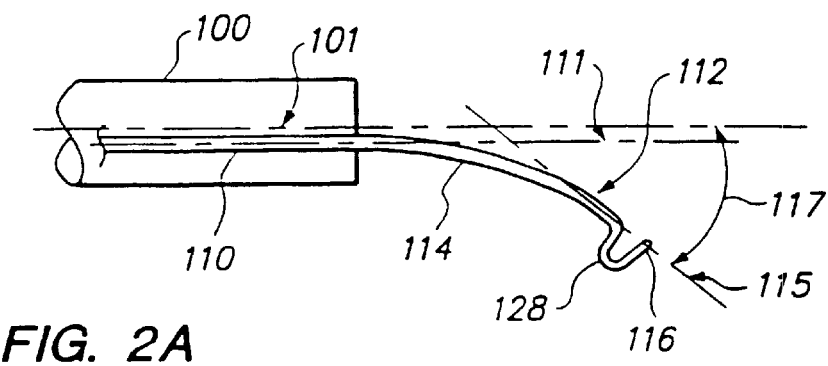
FIG. 2a is a cut-away side view of retractor 112 and cannula 100.

The distal end of the cannula houses a retractor 112, and optionally an endoscope 126 and a surgical tool 120, described below. FIG. 2a illustrates the retractor 112 in more detail. In one embodiment, retractor 112 is formed of resilient wire which has a smooth bend intermediate to a first portion 110 and a second portion 114 of the retractor. The retractor 112 is described as having two portions for ease of description, although the retractor 112 may be formed as an integrated structure. However, retractor 112 may also be manufactured from two separate portions 110, 114 that are coupled together. The first portion 110 of the retractor 112 is positioned within the cannula 100 with the axis 111 of the first portion 110 approximately parallel to the axis 101 of the cannula 100. The second portion 114 is positioned to bend away from the central axis 101 of the cannula. The angle 117 of displacement between the axis 115 of the second portion and the central axis 101 of cannula 100 may be any angle from zero to 180 degrees. The second portion 114 includes a dissection cradle 116 at the distal end of the second portion 114. The retractor 112 may be formed of bioinert material such as stainless steel, or a polymer such as nylon or polyetherimide, or other appropriately strong and resilient plastic. In one embodiment, the retractor 112 includes a coating for lubrication, insulation, and low visual glare using, for example, parylene or nylon 11.

Figure 2B:
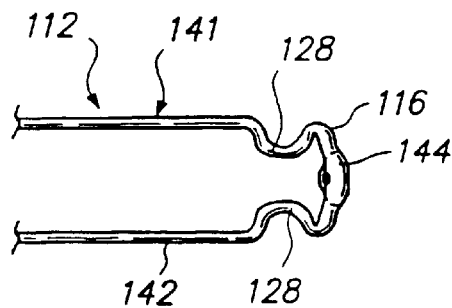
FIG. 2b is a top view of retractor 112.

FIG. 2b illustrates the retractor 112 formed with two legs. The legs 141, 142 of the retractor 112 at the distal end form the dissection cradle 116 in a loop or "U" shape, as shown in FIG. 2a. The top portion 144 of the U-shaped bend is preferably flattened to provide additional surface area for atraumatically supporting a vein 118 or vessel of interest. The side arches 128 of the dissection cradle 116 are used for skeletonizing or dissecting the vein from the surrounding tissues, as well as acting as walls to keep the vessel captured within the arch. The several embodiments of dissection cradle 116 are described in more detail below.

Figure 3A:
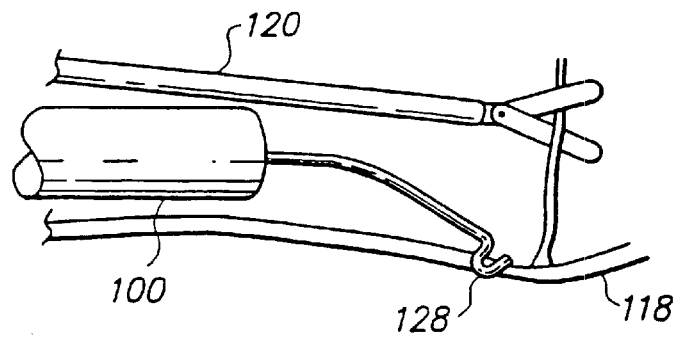
FIG. 3a is a perspective side view of cannula 100 with a sapphenous vein positioned within the cradle 116.

FIG. 3a illustrates a perspective view of the cannula 100 in accordance with the present invention with the retractor fully extended, holding a sapphenous vein 118, and also illustrates an external surgical tool 120 disposed adjacent the cannula 100 for performing a surgical operation, for example, severing a tributary or side branch of the vein 118. The vein is positioned within the side arches 128 of the cradle 116. The dissection cradle 116 may be used to cradle a vein, vessel, tissue or organ of interest, and surgical tool 120 may be any surgical tool suitable for performing a surgical procedure near the dissection cradle 116.

Figure 3B:
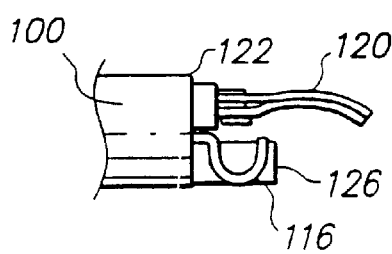
FIG. 3b is a perspective side view of the distal end 122 of cannula 100 in an embodiment in which an endoscope 126 and a surgical tool 120 are present and partially extended.
Figure 3C:
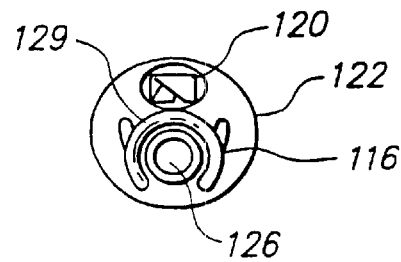
FIG. 3c is a front view of the distal end 122 of cannula 100 in which the surgical tool 120 and the retractor 116 are partially extended, and an endoscope 126 is present.

FIG. 3b illustrates a perspective view of cannula 100 in an embodiment in which the surgical tool 120 is positioned within the cannula 100, and an endoscope 126 is present. In this embodiment, cradle 116 preferably overlays the endoscope 126 with sufficient clearance to facilitate relative movements thereof. However, the endoscope may also be located adjacent the surgical tool 120. In one embodiment, endoscope 126 is positioned with cannula 100 to allow a clear field of view upon extension of the retractor 112. Surgical tool 120 is illustrated as cauterizing scissors, used to sever a tributary or side branch of a sapphenous vein 118. In this embodiment, surgical tool 120 is maximally displaced from the cradle 116 at the cannula end 122. More specifically, as shown in FIG. 3c, the "U"-shaped loop 129 of the cradle 116 is closest to the surgical tool 120. This ensures that a vein 118 or other tissue of interest is retracted away from the surgical tool 120 to facilitate manipulating the surgical tool 120 relative to the side branch or other tissue.

Figure 4A:
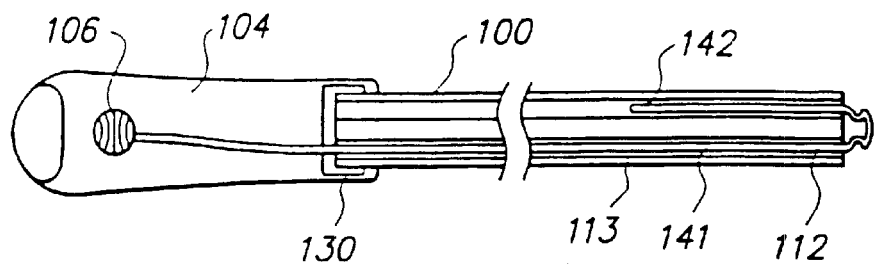
FIG. 4a is a cut-away top view of cannula 100.
Figure 4B:
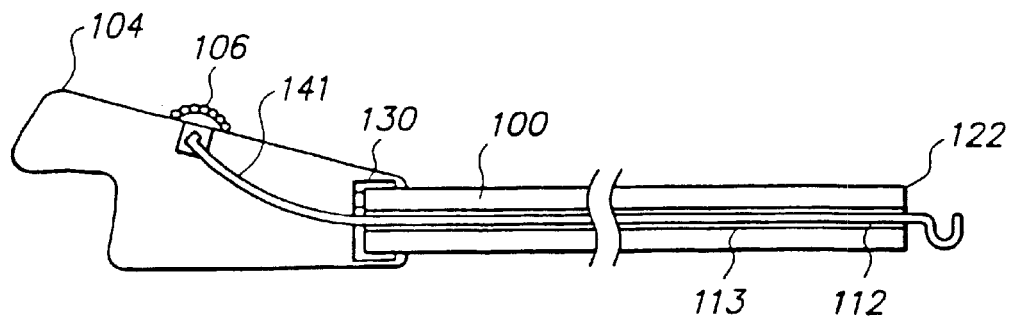
FIG. 4b is a cut-away side view of cannula 100.

FIG. 4a is a cut-away top view of cannula 100. The retractor 112 is slidably positioned within minor lumens 113 along the length of the cannula 100 within close tolerances in order to position the retractor 112 stably within the cannula 100. For example, in one embodiment retractor legs 141, 142 are approximately 0.045 inches in diameter and the lumens 113 encasing the legs 141, 142 are approximately 0.080 inches in diameter, as friction between the legs of the retractor 112 and the lumens 113 holds the retractor stably within the cannula. This configuration restricts rotational movement of the retractor to provide more stable retraction as compared with conventional retractors. The legs 141, 142 of the retractor 112 are formed of flexible, resilient material and are retained within the lumen 113 in substantially straight or flat orientation, but may return to a material bend or curve, as illustrated in FIG. 5a, as the retractor 112 is extended from the distal end of the cannula 100.

The leg 141 of the retractor 112 passes through a sliding gas or fluid seal 130 at the proximal end of the lumen 113. The leg 141 of the retractor 112 passes out of the cannula 100 and into handle 104 for attachment to a slider button 106 for facilitating translational movement of the retractor 112 from the proximal or handle end of the cannula 100. However, other types of control devices such as knobs, grips, finger pads, and the like may be linked in conventional ways to the retractor 112 in order to manually control the translational movement of retractor 112. In one configuration, the proximal end of leg 141 is bent relative to the axis of the cannula, and the button 106 is attached to the bent position of the leg 141 to facilitate moving the button 106 and the retractor 112 translationally under manual control. The button 106 preferably includes lateral grooves to prevent finger or thumb slippage during sliding manipulation of the retractor 112.

Thus, in the operation of a preferred embodiment, a user actuates the slider button 106 to extend retractor 112 out of the lumen 113 at the distal end of the cannula 100. In one embodiment, the resilient retractor 112 is formed in a smooth bend, as shown in FIG. 2a, and gradually deflects away from the central axis 101 of the cannula 100 as the retractor is extended. Upon encountering the target vessel or tissue of interest, the vessel is restrained in the cradle 116, and a lateral resilient force is exerted on the target vessel in a direction away from the cannula. The vessel is thus pushed away from the axis of the cannula 100, isolating it from surrounding tissue or adjacent vessels such as tributaries or side branches. As a tributary is thus isolated, a surgical tool 120 such as cauterizing scissors may be safely employed to operate on the tributary without harming the sapphenous vein 118. When retracted into the cannula 100, the retractor 112 is again resiliently straightened or flattened.

Figure 5A:
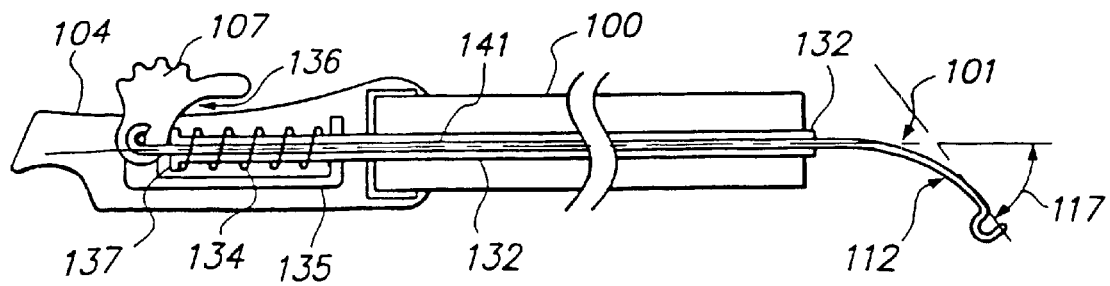
FIG. 5a is a cut-away view of a sliding tube embodiment of cannula 100 in a first position.
Figure 5B:
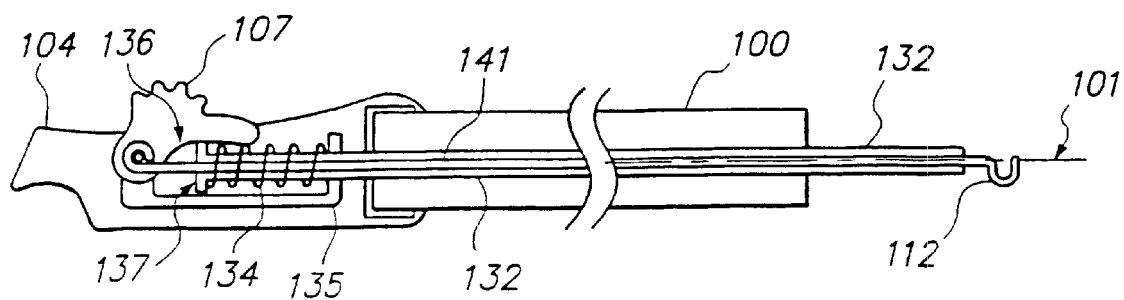
FIG. 5b is a cut-away view of the sliding tube embodiment of FIG. 5a in a second position.

In an alternate embodiment as illustrated in FIGS. 5a and 5b, a sliding tube 132 is added to provide operational versatility to cannula 100. In a first position, the sliding tube 132 is retracted and the retractor 112 protrudes from the distal end at an angle with respect to the central axis 101 of the cannula 100. In a second position, the sliding tube 132 is extended out, temporarily straightening the retractor 112. As illustrated in FIG. 5a, a sliding tube 112, in a first position encases the retractor 112 up to the point at which the retractor 112 curves away from the central axis 101 of the cannula thus allowing the retractor 112 to displace and isolate a target vessel. The proximal end of the sliding tube 132 is linked to button 107 for translationally moving retractor 112 as well as actuating the sliding tube 132. In one embodiment, as illustrated in FIG, 5a, the sliding tube 132 is in a first position with the button 107 in an upright position. A spring 134 is coupled between a support structure 135 and the proximal end 137 of the sliding tube 132. In the first position of sliding tube 132, the spring 134 is extended fully and exerts little or no force on the sliding tube 132. Of course, sliding tube 132 may be manually manipulated without linkage to a button 107.

To extend the sliding tube 100, button 107 is pushed down. As illustrated in FIG. 5b, the button 107 has a cam surface 136 which pushes on the proximal end 137 of the sliding tube 132 as the button 107 is pressed. The sliding tube 132 is pushed forward, overcoming the resilient force of spring 134, to encase the retractor 112 and decrease angle 117 between the distal end of the retractor 112 and the central axis 101 of the cannula 100. Upon releasing the button 107, the spring force urges the proximal end 137 of the sliding tube 132 back toward the first position against button 107. The sliding tube 132 is formed of material having sufficient strength to force the retractor 112 to straighten out the angle 117, and the retractor 112 is formed of resilient material having a sufficient flexibility to straighten out the angle 117 in response to a tube 132 being slid over the retractor 112, but having sufficient rigidity to cradle and dissect a target vessel. Resiliency of the retractor 112 ensures return to the downwardly-curved shape after being released from tube 132. Thus, in accordance with this embodiment, a user may employ the curved retractor for certain applications and employ the straightened form for other applications. A manual actuator may be configured in other ways than button 107 to extend the sliding tube 132 in response, for example, to being pulled up instead of pushed down.

Figure 6A:
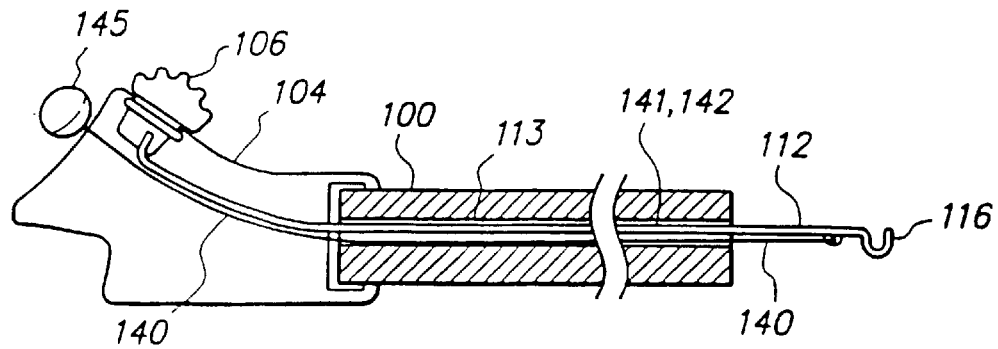
FIG. 6a is a cut-away view of an embodiment of cannula 100 having an angling device 140.
Figure 6B:
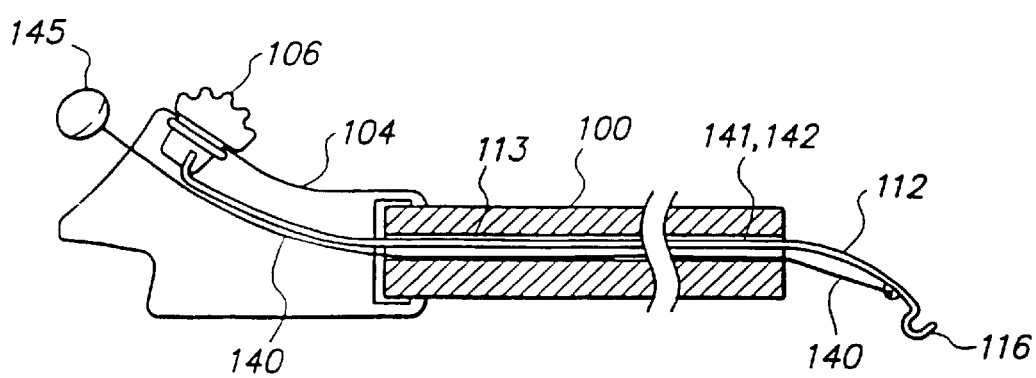
FIG. 6b is a cut-away side view of the apparatus illustrated in FIG. 6a in which the retractor 112 is extended and the angling device 140 is actuated.

Another embodiment employs a retractor 112 which has a naturally straight shape. As illustrated in FIGS. 6a and 6b, an angling device 140 is disposed between the distal end of the retractor 112 and the proximal end of the cannula. The angling device 140 may be positioned within the same lumens 113 as the retractor 112 and preferably may comprise two wires coupled to points below the cradle 116 of the retractor 112 substantially in parallel positions on each of the legs 141, 142.

Figure 6C:
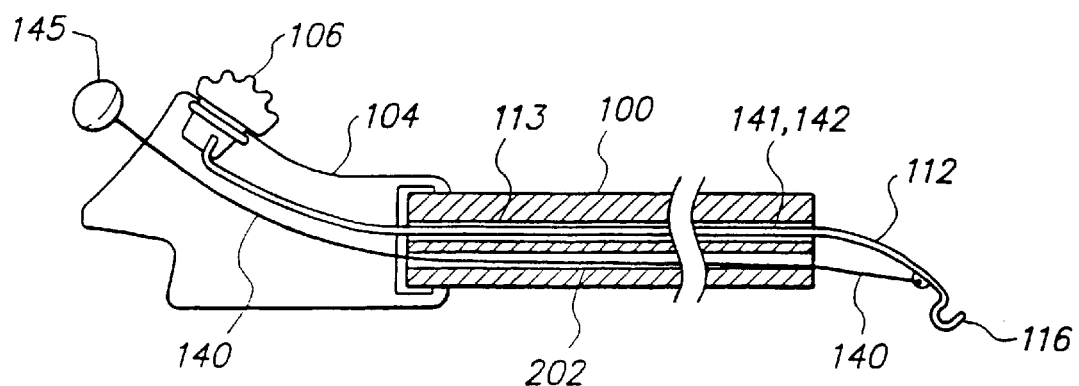
FIG. 6c is a cut-away side view of the angling device embodiment in which the angling device 140 is in a separate lumen from the retractor 112.

Upon extending the retractor 112 using button 106, the angling device 140 is extended with the retractor 112. The angling device 140 is coupled to a handle 145 at the proximal end of the cannula 100 to facilitate establishing an angle in the retractor 112 by pulling with a backward force on the angling device 140. As illustrated in FIG. 6b, after the retractor 112 is extended, the angling device 140 is actuated and a bend is created in the retractor 112 as the backward force exerted on the distal end of the retractor is exerted against the relatively fixed position of the retractor legs 141, 142 disposed within the lumens 113. As shown in FIG. 6c, the angling device 140 may also be located in a separate lumen 202 from the retractor 112 with part of the angling device 140 positioned outside of the cannula 100 when the retractor 112 is in the retracted position.

Figure 7A:
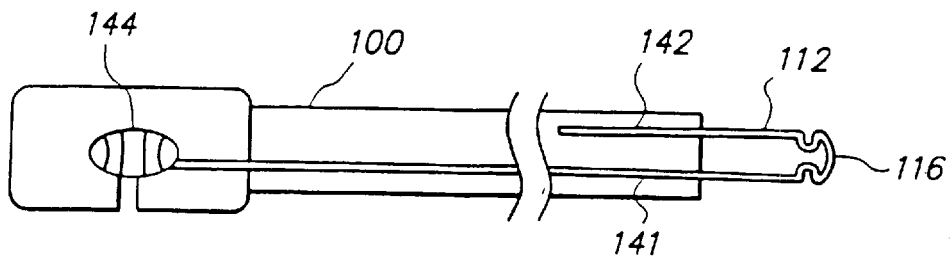
FIG. 7a is a cut-away side view of a twistable retractor 112 in a straight position.
Figure 7C:
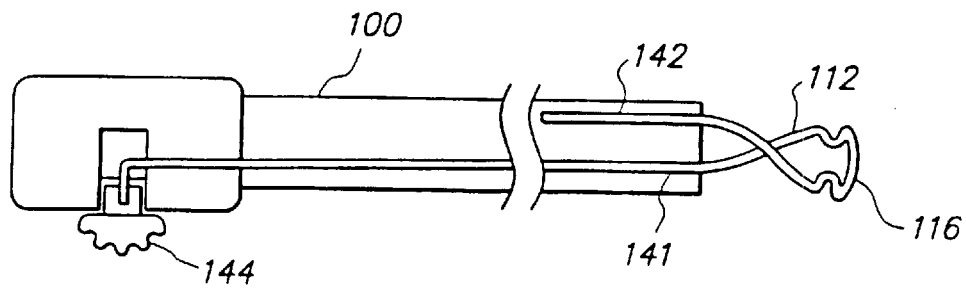
FIG. 7c is a cut-away side view of twistable retractor 112 in a crossed position.
Figure 7B:
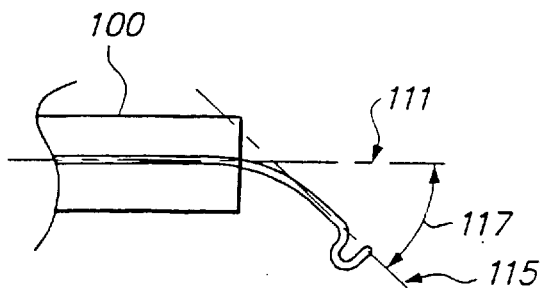
Figure 7D:
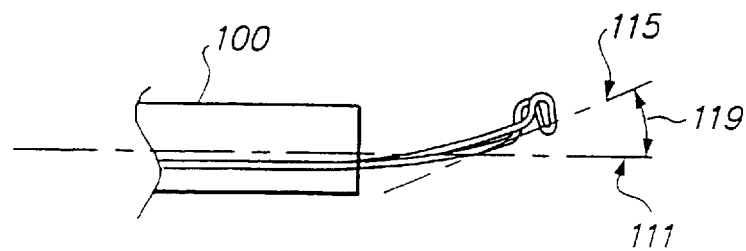
FIG. 7d is a side view of the retractor 112 of FIG. 7c.

FIG. 7a illustrates another embodiment of cannula 100 in which the retractor 112 is pre-formed with one leg 141 of the retractor 112 bent at an angle at its proximal end skewed to the axis of the distal end of the other leg 142. The bent portion of the leg 141 may be linked to a sliding knob 147 for convenient manual manipulation of this embodiment of the invention. Upon sliding the knob 147, the leg 142 coupled to knob 147 is twisted rotationally. The two legs 141, 142 of retractor 112 are coupled together via cradle 116. The axis of the second portion of the retractor 112 in the first position is at a first angle 117 to the axis of the cannula 100, as shown in FIG. 7b. As knob 147 is moved, leg 141 is rotated and crosses under leg 142, as shown in FIG. 7c. This causes cradle 116 to flip 180 degrees and bends the retractor 112 at a second angle 119, as shown in FIG. 7d. Thus, if a vessel is disposed on one side of cradle 116 or cannula 100 while the retractor 112 is in the first position, then upon rotating the knob 147, the vessel is transported to the other side of the cannula 100. This allows the user to isolate the vessel by simply actuating knob 147.

Figure 8A:
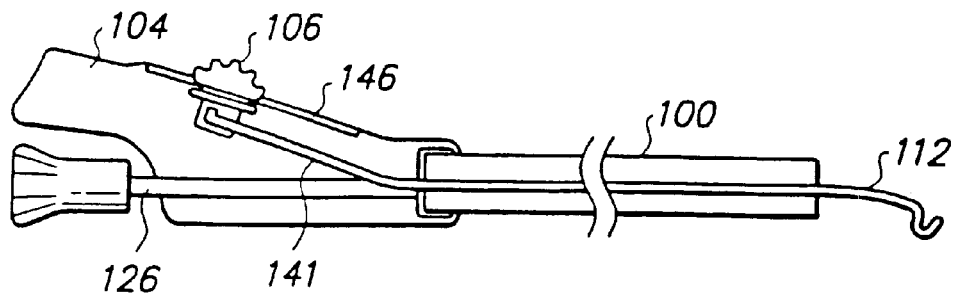
FIG. 8a is a cut-away side view of the handle 104.
Figure 8B:
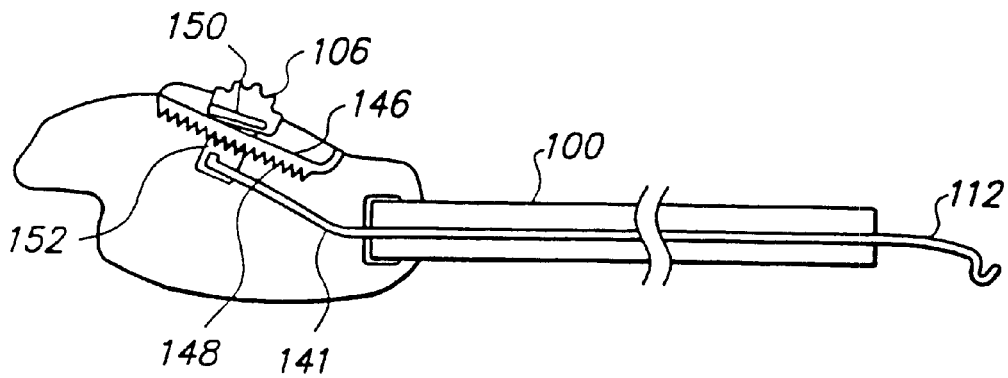
FIG. 8b is a cut-away side view of an alternate embodiment of handle 104.

FIG. 8a illustrates a cut-away side view of button 106 on the handle 104 of cannula 100, with an endoscope 126 positioned within cannula 100. As mentioned above, button 106 is coupled to one leg 141 of the proximal end of retractor 112. Sliding the button 106 in groove 146 translationally moves the retractor 112. Groove 146 is preferably minimally wider than the shaft of button 106 to minimize excessive horizontal movement of button 106 while still allowing smooth translational movement of button 106. As illustrated in FIG. 8b, the button 106 may include locking or ratcheting teeth 152 to give tactile feedback of its location, and to positively retain the button and the associated leg 141 in an extended or retracted position. Several mating teeth 148 are located underneath groove 146, and a spring member 150 is attached to button 106 to exert pressure against the base of groove 146, to engage mating teeth 148, 152. When a force is applied on the top of button 106, the interlocking sets of teeth are disengaged and button 106 can move freely. Upon achieving the desired extension or retraction of the leg 141, button 106 is released and is retained place by the engaged teeth 148, 152.

Figure 9A:
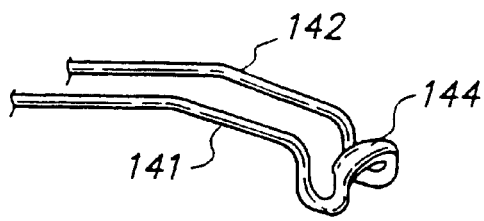
FIG. 9a is a side view of cradle 116.

FIG. 9a illustrates a top view of cradle 116 in an embodiment in which the cradle 116 is formed by two legs 141, 142 of retractor 112. The distal end of the legs form "U"-shaped side guides. The top 144 of the distal portion of the "U" is preferably flattened. This provides atraumatic support for the target vessel retained within cradle 116. Additionally, by minimizing the thickness of distal portion 144, contact with other devices in close proximity with retractor 112 is minimized.

Figure 9B:
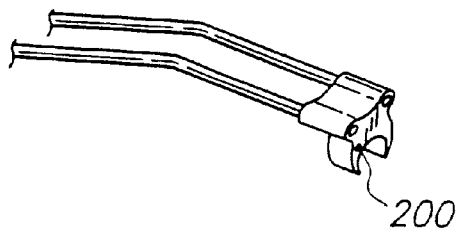
FIG. 9b illustrates a first alternate embodiment of cradle 116.

The cradle 116 may have other effective shapes, for example, as illustrated in FIG. 9b in which a "C" ring element is attached to legs of the cradle 116. The "C" ring may have a small hole 200 in one side with an axis approximately parallel to the axis of the retractor 112. This hole 200 is used to hold suture or other ligating materials, and may also be used as a knot pusher. As shown in FIGS. 10a and 10b, in an alternate embodiment of the embodiment of FIG. 9b, the retractor 112 is formed and flattened and a "C"-shaped ring is coupled to the retractor 112 by, for example, gluing or molding the "C" ring to the distal end of the retractor 112, as shown in FIG. 10c and 10d.

Figure 9C:
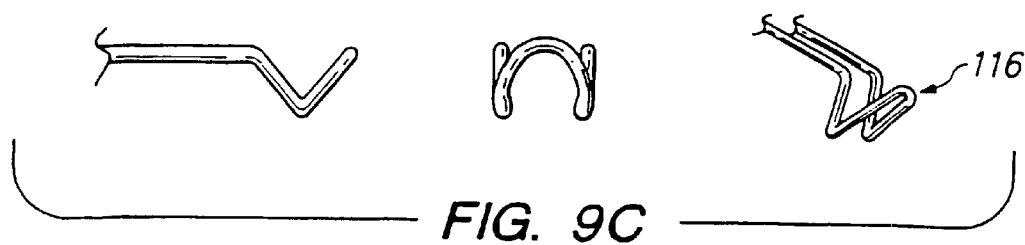
FIG. 9c illustrates multiple views of a second alternate embodiment of cradle 116.
Figure 9D:
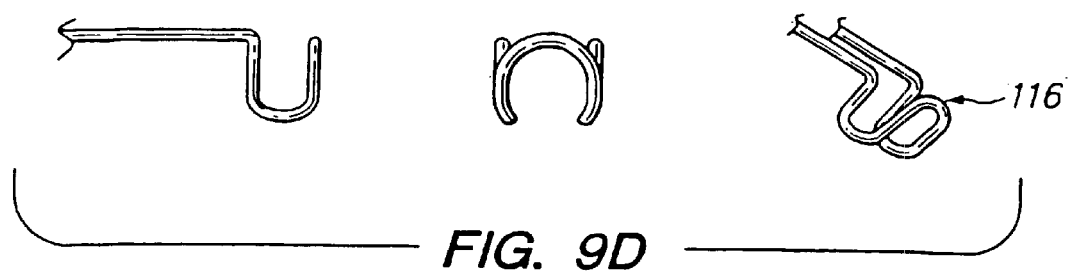
FIG. 9d illustrates multiple views of a third alternate embodiment of cradle 116.
Figure 9E:
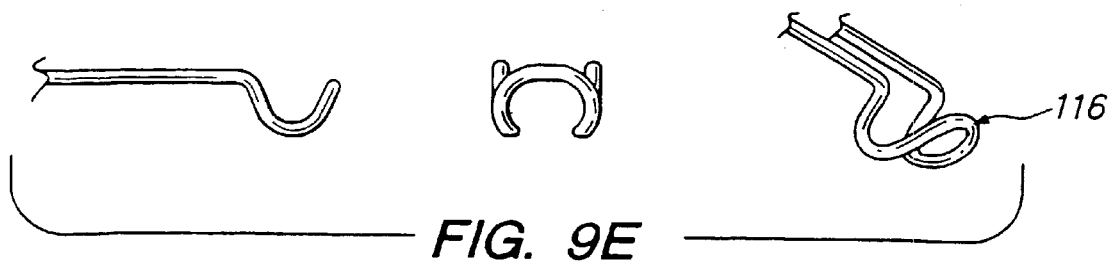
FIG. 9e illustrates multiple views of a fourth alternate embodiment of cradle 116.

Referring back to FIGS. 9c, 9d, and 9e, the side guides of the cradle may include a loop 129 in a "V" shape, an arced "U" shape, or a semi-circular shape. In one embodiment, as illustrated in FIG. 9f, the retractor 112 has only one leg 141, and the cradle 116 is formed by the leg 141. A stopper 160 is coupled to the end of the leg 141 to serve as a guide to retain the target vessel, and add a blunt surface to the end of the wire, for example, for pushing and probing tissue. FIG. 9g illustrates a retractor 112 having a spur 204 formed in one or both legs 141, 142 for allowing the retractor 112 to be used for dissection. Sinusoidal, half-sinusoidal, and other geometric configurations may be used equally effectively as the shape of loop 129 in accordance with the present invention.

Figure 11A:
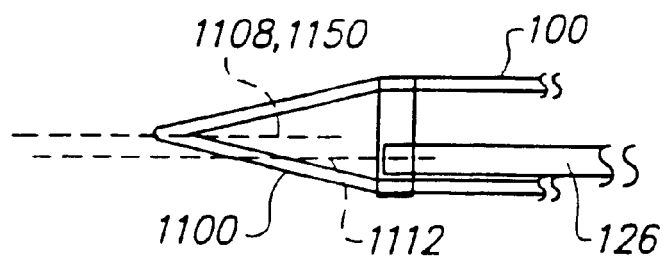
FIG. 11a illustrates a cut-away side view of a tip 1100 in a cannula housing an endoscope 126.
Figure 11B:
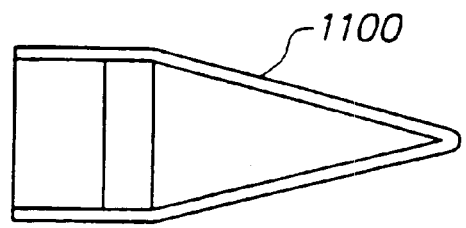
FIG. 11b illustrates a side view of the tip 1100 isolated from cannula 100.

FIG. 11a illustrates a tip 1100 for use with a multi-lumen cannula 100 housing an endoscope 126. The tapered tip 1100 may be removed from, and reattached to the distal end of a cannula 100, as desired. Upon attachment, the tip 1100 seals the distal end of a cannula 100 in a fluid-tight manner. The tip 1100 is configured to provide dissection of the tissue surrounding the vessel of interest, and has a distal radius of approximately 0.045" to reduce the hazard of penetrating the vessel of interest. The inner surface of the tip 1100 tapers to a sharp interior point and a slightly rounded exterior point and the tip 1100 has a uniform wall thickness. The tip 1100 preferably has taper angles of approximately 15° which provides a maximal, undistorted, visual field through an endoscope 126. The tip 1100 tapers outward to a maximal diameter of about 12¾ mm at its shoulder to cover the cannula 100 body which also has a diameter of about 12¾ mm. All of these features allow the tip 1100 to effectively dissect tissue. The tip 1100 of FIG. 11a has a central axis 1150 aligned with the central axis 1108 of the cannula 100. The visual field provided by the endoscope 126, although satisfactory for surgical procedures, is not complete because the endoscope 126 is in a lumen that is offset from the central axis 1108 of the cannula 100. The endoscope 126 is offset because of the space required inside the cannula 100 for housing retractors and other instruments in adjacent lumens. FIG. 11b illustrates this tip 1100 detached from the cannula 100.

Figure 12A:
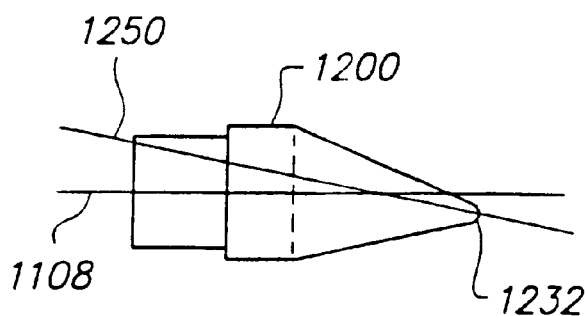
FIG. 12a illustrates a side view of an offset tip 1200 in accordance with the present invention.

FIG. 12a illustrates an offset tip 1200 for a cannula 100 in accordance with the present invention. The offset tip 1200 is a transparent, tapered tip as described above for use in endoscopic dissection of a vessel. However, in this embodiment the axis 1250 of the tip 1200 is skewed relative to the central axis 1108 of the cannula 100. The axis 1250 of the tip 1200 is skewed approximately 8°, an angle that is chosen to align the apex 1232 of the tip 1200 with a central axis 1112 of the endoscope 126, as shown in more detail in FIG. 12b.

Figure 12B:
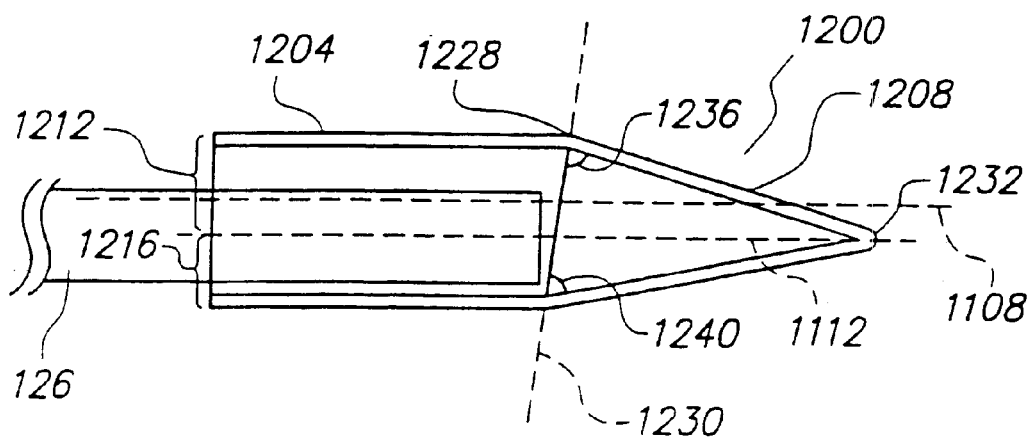
FIG. 12b illustrates a cut-away side view of the offset tip 1200 in a cannula 100 housing an endoscope 126.

FIG. 12b illustrates the offset tip 1200 housed in cannula 100 in more detail. The cannula 100 houses a 5 mm endoscope 126 having a central axis 1112 eccentric to the central axis 1108 of the cannula 100. In order to bring the distal end or apex 1232 of the axis of the tapered tip 1200 into the center of the visual field along the central axis 1112 of the endoscope 126, the tapered tip 1200 is tilted or inclined by approximately 8° toward the lumen housing the endoscope 126. This allows the apex 1232 of the tip 1200 to approximately intersect with the central axis 1112 of the endoscope 126. As illustrated in FIG. 12b, the tip 1200 is inclined toward the central axis 1112 of the endoscope 126 without altering the taper angles 1236 and 1240 of the side walls. This is accomplished by forming a transition 1228 between the proximal or cylindrical portion 1204 of the tip 1200 and the distal or conical portion of the cannula body 1208 of the tip 1200 substantially along a plane 1230 that is skewed from normal to the central axis 1108 of the cannula 100. The distal portion 1208 of the tip 1200 retains its conical shape and equal taper angles 1228, 1236 between the side walls and the transition plane. The slight extension of the cannula body at the transition plane provides sufficient incline to allow the apex 1232 of the tip 1200 to intersect the central axis 1112 of the endoscope 126. The tip 1200 may be formed of separate conical and cylindrical parts that are attached together, or the tip 1200 may be formed as an integrated structure in the shape thus described.

Figure 12C:
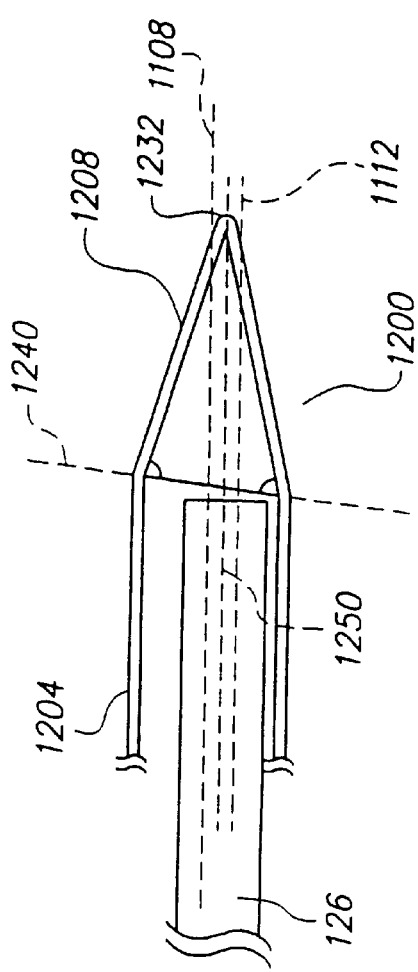
FIG. 12c illustrates a cut-away side view of an alternate embodiment of offset tip 1200.

Alternatively, as shown in FIG. 12c, the tip 1200 is inclined at a lesser angle, for example, 5 degrees, toward the axis 1112 of the endoscope 126, positioning the axis 1250 of the distal end 1232 of the tip 1200 intermediate between the central axis 1108 of the cannula 100 and the axis 1112 of the endoscope 126. Positioning the axis 1250 of the tip 1200 to this intermediate point allows the retention of steep conical angles in the tip 1200 which allow for easier advancement of the cannula 100 while using a minimal amount of force. The intermediate positioning also provides a more complete visual field as seen through endoscope 126.

Figure 13:
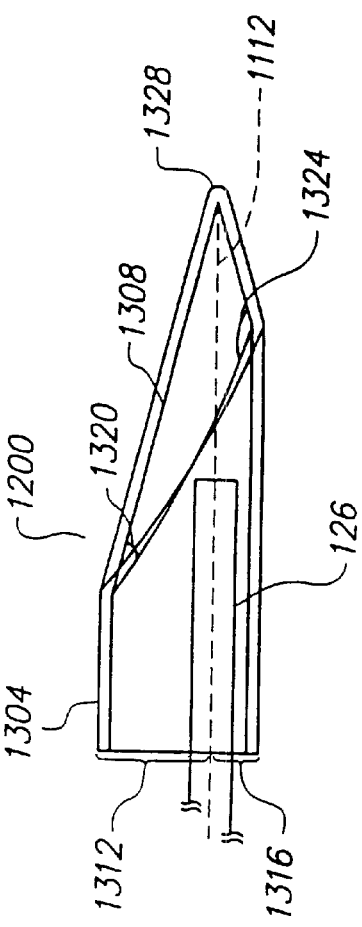
FIG. 13 illustrates a cut-away side view of an alternate embodiment of the offset tip 1300.

An alternate embodiment of an offset tip 1200 is shown in FIG. 13 in which the taper angles 1320, 1324 of the side walls are selected to form the apex 1328 of the tip 1200 aligned with the central axis 1112 of the endoscope 126. As illustrated, the lower region 1316 of the cylindrical part 1304 extends beyond the upper region 1312 of the cylindrical part at a plane of transition between cylindrical and tapered regions of the tip. However, in this embodiment, the taper angles 1320, 1324 are not equal and the thirty degree angled conical configuration of the tapered part 1308 is not maintained. Rather, the lower taper angle 1324 is increased to an obtuse angle and the upper taper angle 1320 is a reduced acute angle relative to the plane of transition between the cylindrical and tapered portions of the tip. In this configuration of the conical portion 1308, the apex 1328 of the tip 1200 aligns with the central axis 1112 of the endoscope 126. Thus, in accordance with either embodiment, a tip 1200 is provided which allows a maximal visual field to be viewed by the surgeon via the endoscope 126 that is eccentric the central axis 1108 of the cannula 100, but that is aligned with or near to the apex 1232 of the tip 1200.

Figure 14A:
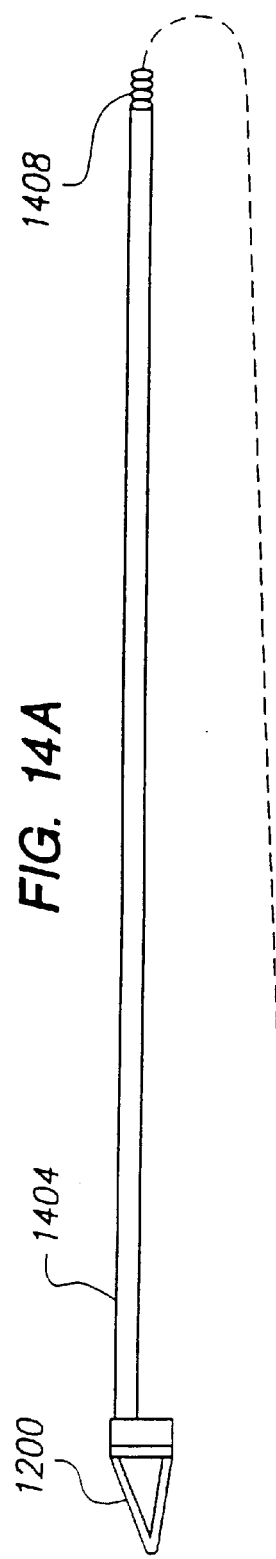
FIG. 14a illustrates a perspective side view of the offset tip 1200 and mounting rod 1404.
Figure 14B:
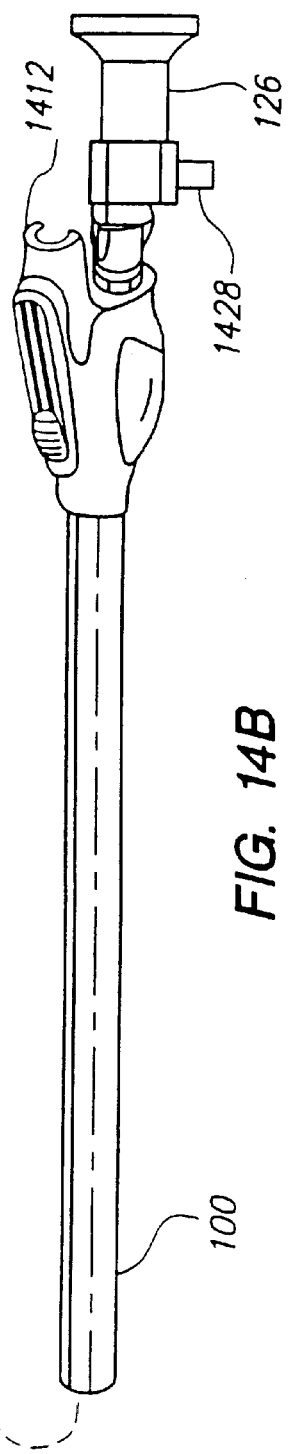
FIG. 14b illustrates a perspective side view of cannula 100 for housing offset tip 1200 and mounting rod 1404.
Figure 14C:
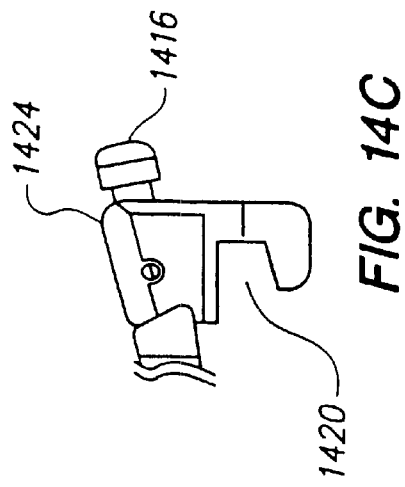
FIG. 14c illustrates a perspective side view of offset tip housing 1424 at the proximal end of the cannula 100.
Figure 14D:
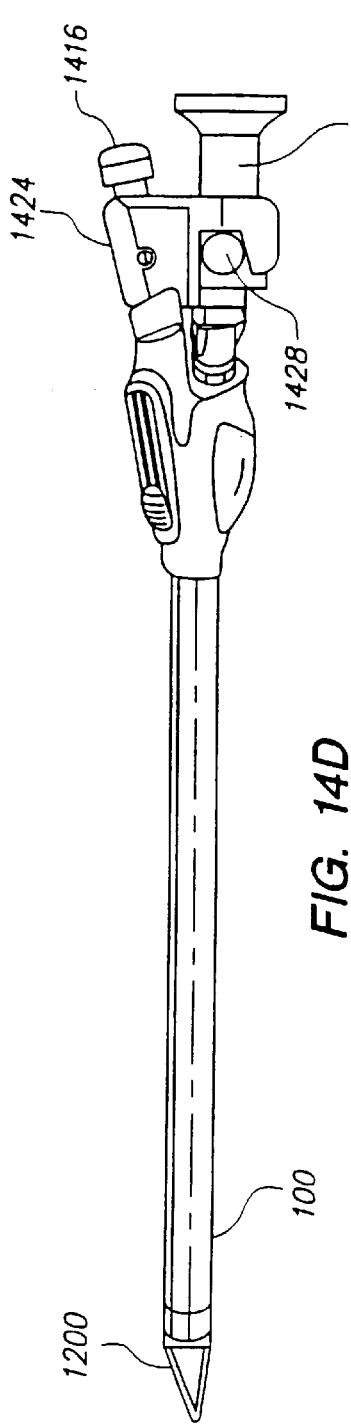
FIG. 14d illustrates a perspective side view of cannula 100 with offset tip 1200 and offset tip housing 1424.

FIG. 14a illustrates a perspective side view of the offset tip 1200 and mounting rod 1404. The tip 1200 is attached to the cannula 100 via the long rod 1404 which extends through an eccentric lumen of the cannula 100, as shown in FIG. 14b, and the apex of the tip 1200 is tilted away from the rod 1404 and towards the endoscopic lumen (not shown). The elongated rod 1404 may be attached to the tip 1200, or may be constructed as an integral part of the tip 1200. The elongated rod 1404 preferably is secured in housing 1424, shown in FIG. 14c, via threads 1408 on the proximal end of rod 1404 and mating threads within nut or knob 1416. The rod 1404 and housing 1424 abut against the proximal end of the cannula handle 1412, as illustrated in the perspective side view of the assembled device shown in FIG. 14d. Referring back to FIGS. 14a–c, the housing 1424 includes a slot 1420 configured to slip over the light cable outlet 1428 on the endoscope 126 as assembled within the cannula 100. The housing 1424 preferably contains a rotating nut 1416 which accepts the threaded proximal end 1408 of the rod 1404. When tightened onto the rod 1404, as shown in FIG. 14d, the housing 1424 prevents the cannula 100 from rotating about the endoscope 126 by holding the endoscope 126 fixed with respect to the handle 1412. This allows the operator to maintain the correct orientation of the endoscope 126 on the vessel. If the endoscope 126 is allowed to rotate freely, the image may turn sideways or upside down without the operator realizing it, and injury may occur to the vessel if the cannula 100 is advanced in the wrong direction.

Figure 14F:
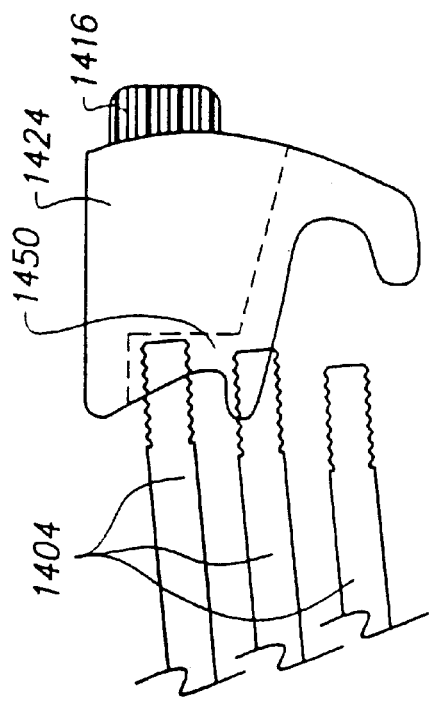
FIG. 14f illustrates a cut-away side view of the offset tip mounting 1424 of FIG. 14e.
Figure 14E:
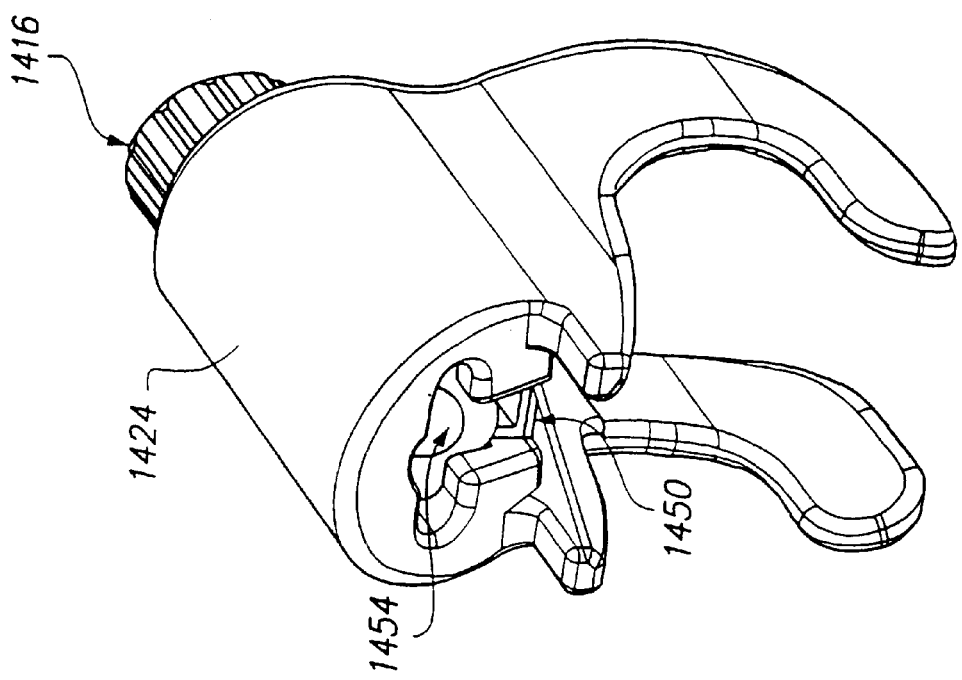
FIG. 14e illustrates a perspective side view of an alternate embodiment of offset tip mount 1424.

In one embodiment, as shown in FIGS. 14e and 14f, the elongated rod 1404 slips into the housing 1424 via a groove 1450 near its proximal end, and passes through the main hole 1454 in the housing 1424. The groove 1450 allows for the housing 1424 to cover the proximal end of the mounting rod 1404 without completely clearing the most proximal tip of the mounting rod 1404. This allows more room for attaching the housing 1424 which lies between the elongated rod 1404 and additional optical components. The rod 1404 may contain an elastic section, or the rod 1404 may be somewhat elastic along its entire length to facilitate stretching the rod 1404 and pulling it into position in the slot 1454 on the housing 1424, while locking the tip 1200 in place. The elastic force also facilitates sealing the tip 1200 against the distal face of the cannula body.

FIGS. 15a and 15b illustrates an alternate embodiment of offset tip 1200 and cannula 100. In this embodiment, offset tip 1200 is formed with an elongated case 1500 which slides over the cannula body 100 and locks to the proximal end of cannula 100. In this embodiment, proximal end of cannula 100 is threaded and allows a threaded proximal section of elongated case 1500 to mate securely to the cannula 100.

In a surgical procedure using the tissue-dissecting cannula of the present invention, the surgeon first incises 1600 the skin overlying a vessel of interest to expose the vessel as an initial step of the procedure illustrated in the flow chart of FIG. 16. A scissor tool is inserted 1602 into the incision to create a path to the vessel by dissecting the overlying tissue. Next, the tip 1200 of the cannula 100 is inserted 1604 into the incision to bluntly dissect tissue to form an initial tunnel along the vessel from the incision. The incision is then sealed 1608 using a blunt tip trocar and a tunnel is insufflated 1612. The cannula is advanced 1616 along the vessel to dissect tissue adjacent the vessel under endoscopic visualization through the transparent tip. The offset tip 1200 with the apex thereof in alignment with the endoscope 126 provides a full visual field for the surgeon as the cannula 100 is advanced. The conical end of the tip 1200 dissects the tissue as the cannula 100 is advanced along the vessel. The surgeon dissects both on the anterior and posterior sides of the vessel to create a full 360 degree tunnel around the vessel. Once a selected surgical site is reached, the cannula 100 is removed 1620 from the incision seal and the tip 1200 is removed 1624 from the cannula 100. In one embodiment, as described above, the tip 1200 is removed by unscrewing the threaded portion 1408 of the rod 1404 from the rotating nut 1416. The tip housing 1424 itself is also removed in this embodiment. Insufflation is maintained and the cannula 100 without tip 1200 is inserted 1628 into the seal into the tunnel adjacent the vessel. Transecting devices are then inserted 1630 into the cannula 100. Without tip 1200 disposed over the distal end, the cannula 100 can now be used for transecting 1632 side branches and the ends of the vessel of interest using endoscopic instruments that are selectively installed and removed within instrument lumens in the cannula body 100. After these procedures are completed, the vessel may be removed 1636.

Figure 17C:
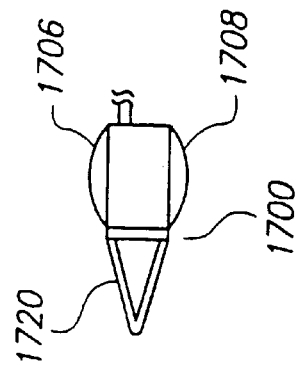
FIG. 17c illustrates a top view of an alternate embodiment of offset tip dilator 1700.
Figure 17A:
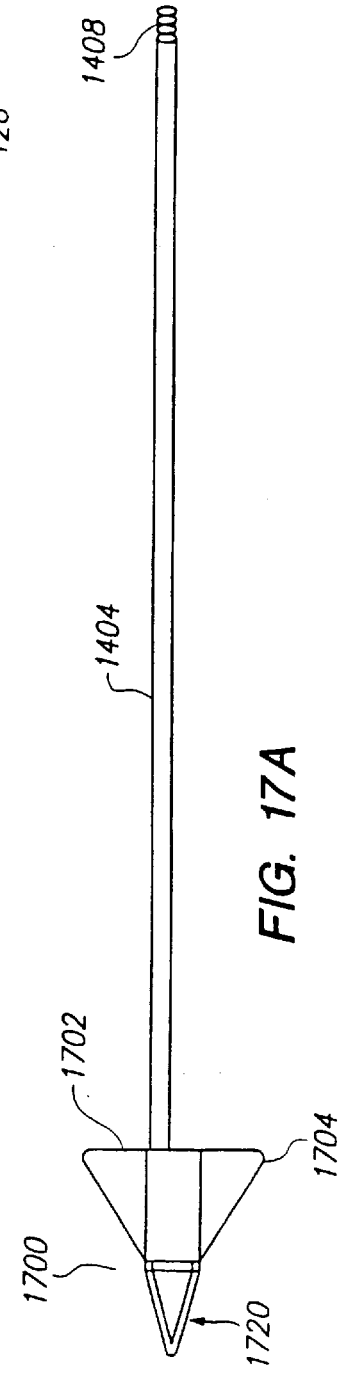
FIGS. 17a illustrates a top view of an embodiment of an offset tip dilator 1700 according to the present invention.
Figure 17B:
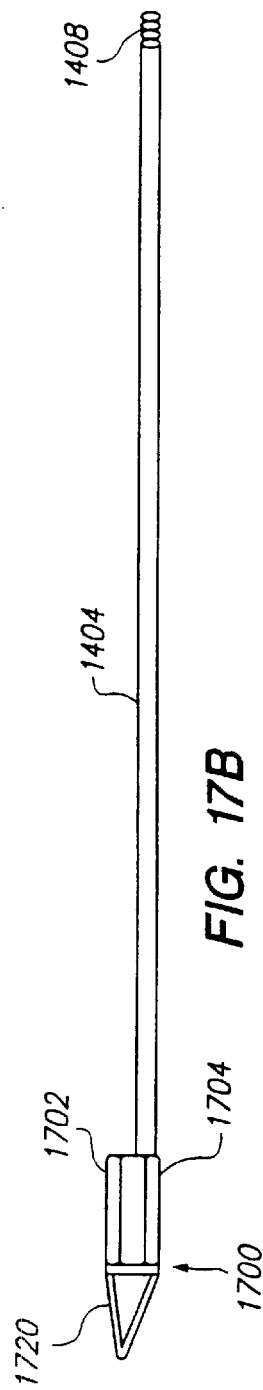

FIG. 17a illustrates another embodiment of an offset tip dilator 1700. In this embodiment of the present invention, the tip 1700 also includes wing-like protrusions for enlarging or dilating a peri-vascular cavity in the course of separating a vessel from adjacent connective tissue. For example, after tissue dissection with an offset tip 1200 to form a tunnel or working cavity adjacent a target vessel by dissecting along the anterior and posterior sides of the vessel, the cannula 100 is removed from the distal end of the body, the offset tip 1200 is detached, and a second tip 1700 is attached to the distal end of the cannula body 100. In one embodiment, the second tip 1700 includes a transparent tapered tip with planar wing-like protrusions or extensions disposed proximal to the distal end 1720 of the tip 1700. The wing-like protrusions 1702, 1704 each include a swept back leading edge. As shown in FIG. 17b, the tip 1200 is tilted away from the mounting rod 1404 to align with the central axis of an endoscopic lumen (not shown). The wing-like protrusions 1702, 1704 may also include curved distal and proximal edges, for example, in a parabolic configuration as shown in FIG. 17c, providing a smoother withdrawal of the cannula 100 from the insufflated tunnel. The tip 1700 attaches to the cannula body 100 in the same manner as previously described with reference to the offset tip 1200, with an elongated rod 1404 extending through a lumen of the cannula 100 and locking at the proximal end of the handle 1412. The cannula 100 may thus be advanced through tissue under full-field endoscopic visualization through the tapered tip 1720 with the wing-like protrusions 1702, 1704 extending substantially diametrically to facilitate tunnel dilation.

The wing-like protrusions 1702, 1704 of the tip 1700 are arranged in substantially planar geometry in contrast to the solid bulbous, oval element described above. The planar configuration of the wing-like protrusions 1702, 1704 substantially reduce the frontal profile of the dilator required to penetrate tissue, and thus reduces the resistive force encountered during advancement of the cannula 100 through tissue. Although the tissue-dilating force is exerted on tissue surrounding the cavity in a bilateral, substantially planar orientation by the outer edges of the wing-like protrusions 1702, 1704 that dissect tissue forming the cavity walls, the dilated cavity may retain a round cross-section for example, within an insufflated cavity, in the same manner as if tissue dilation was performed using a solid oval dilator that applies dilating force circumferentially.

Figure 18:
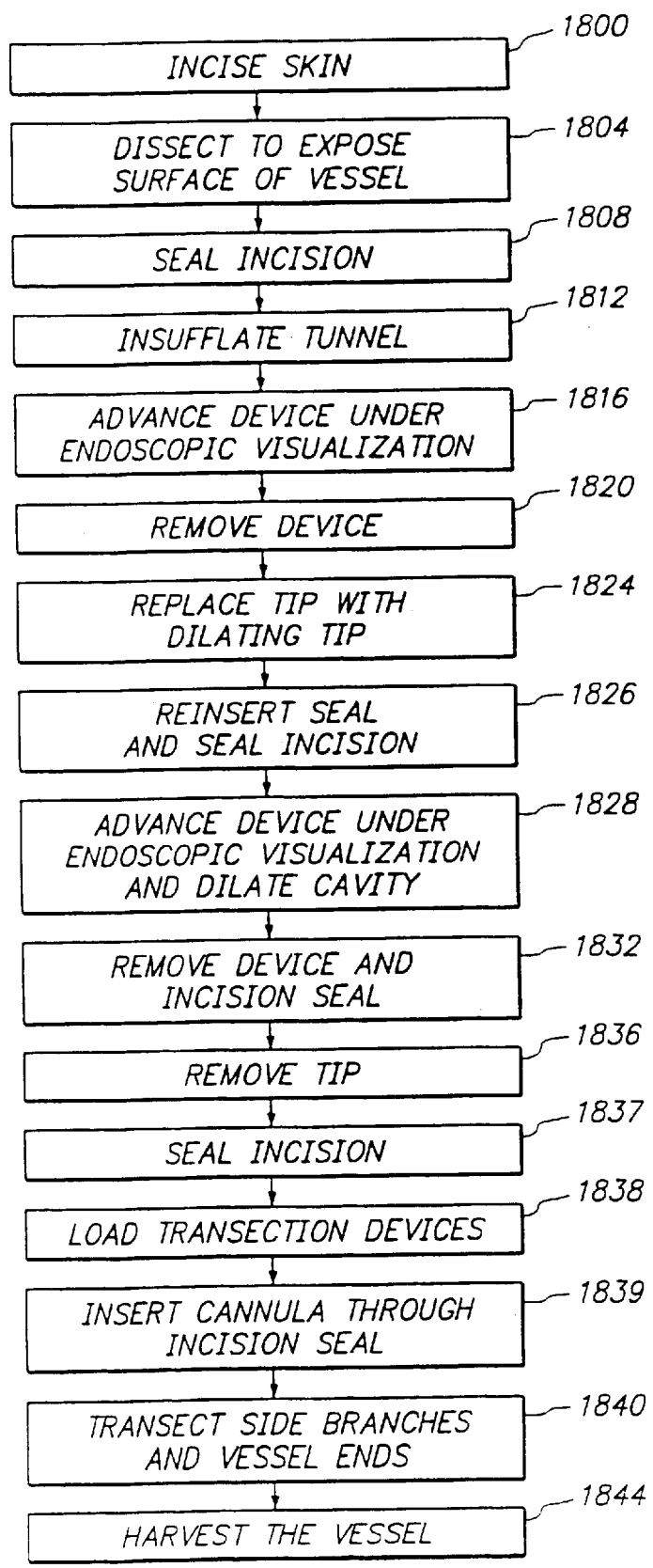
FIG. 18 is a flow chart illustrating a method of dilating tissue in accordance with the present invention.

FIG. 18 illustrates a method of dilating tissue in accordance with one method embodiment of the present invention. The skin is incised 1800 overlying the vessel of interest, and the scissor tool is inserted into the incision to create a path to the vessel by dissecting the overlying tissue. The incision is then bluntly dissected 1804 using the offset tip 1200 to expose the vessel surface. The incision is sealed 1808 and a tunnel is insufflated 1812. The cannula 100 is advanced 1816 along the vessel under endoscopic visualization through the transparent tip 1200. After sufficient length of tunnel is formed adjacent the vessel, the cannula 100 is removed 1820 and the incision seal is removed or slid backwards to the proximal end of the cannula 100. The offset tip 1200 is then replaced 1824 with the dilating tip 1700. The seal is reinserted and the incision is sealed 1826. The cannula 100 is advanced 1828 and the cavity is further dilated responsive to the advancement of the planar wing-like protrusions 1702, 1704 through tissue forming the tunnel walls. The cannula 100 is removed 1832 a second time, and the incision seal is again removed or slid backwards to the proximal end of the cannula 100. The dilating tip is removed 1836 and the incision is sealed 1837. Transection devices are loaded 1838 through instrument lumens within the cannula body 100 into the cannula 100 and the cannula 100 is then inserted 1839 back into the incision. Without any tip covering the distal end of the cannula 100, the vessel side branches and ends are transected 1840 using endoscopic instruments, and the vessel is then removed 1844 from the dilated tunnel.

What is claimed is:

1. A surgical apparatus comprising:
    an elongated cannula having an instrument lumen for supporting a surgical instrument and an endoscopic lumen for supporting an endoscope, the endoscopic lumen having a central axis eccentric to a central axis of the cannula;
    a transparent tip positioned at a distal end of the cannula, having tapered walls converging toward a distal end that is substantially aligned with the central axis of the endoscopic lumen for providing visualization through the transparent tip via an endoscope within the endoscopic lumen;
    the tip including a mounting rod attached to a proximal end of the tip and including a mounting structure disposed at a proximal end of the mounting rod to engage the proximal end of the cannula for securing the tip at the distal end of the cannula.

2. The surgical apparatus of claim 1 wherein the tip further comprises:
   a cylindrical proximal portion; and
   a conical end portion, wherein the conical end portion has unequal taper angles relative to a plane of transition between the cylindrical and conical portions of the tip, for aligning the distal end of the conical portion with the central axis of the endoscopic lumen.

3. The surgical apparatus of claim 1, wherein the tip further comprises:
   a conical portion, positioned at a distal end of the tip; and
   a mounting rod, attached to a proximal end of the conical portion, having a locking section disposed at a proximal end of the mounting rod.

4. The surgical apparatus according to claim 1 in which the mounting rod is flexible and extends through a lumen in the cannula that is skewed relative to the endoscopic lumen near a proximal end thereof.

5. The surgical apparatus of claim 1 in which the tip further comprises:
   a proximal portion for attachment to a distal end of the cannula; and
   a distal portion including the distal end disposed forward of the proximal portion to form a transition plane between the proximal and distal portions skewed from the normal to central axis of the cannula for positioning the distal end of the distal portion in substantial alignment with the central axis of the endoscopic lumen.

6. The surgical apparatus of claim 5, wherein the proximal portion of the tip further comprises:
   a cylindrical tube, having an upper region and a lower region, in which a distal end of the upper region extends beyond a distal edge of the lower region; and
   the distal portion of the tip further comprises:
   a conical end, having an upper and lower region, in which a proximal end of the lower region extends proximally beyond a proximal edge of the upper region.

7. The surgical apparatus of claim 5 wherein taper angles formed relative to the plane of transition between the cylindrical tube and the conical end are substantially equal.

8. A surgical apparatus comprising:
   an elongated cannula having an endoscopic lumen for supporting an endoscope, the endoscopic lumen having a central axis eccentric to a central axis of the cannula;
   a transparent tip positioned at a distal end of the cannula, having tapered walls converging toward a distal end that is substantially aligned with the central axis of the endoscopic lumen, for providing visualization through the transparent tip via an endoscope within the endoscopic lumen;
   the tip including a mounting rod attached to a proximal end of the tip and including a mounting structure disposed at a proximal end of the mounting rod; and
   the cannula comprises:
   a mating structure, disposed near a proximal end of the cannula for mating with the mounting structure near the proximal end of the mounting rod to retain the tip on the distal end of the cannula.

9. The surgical apparatus according to claim 8 in which the mounting structure of the mounting rod includes threads thereon for mating engagement with the mating structure disposed near the proximal end of the cannula.

10. An apparatus for dilating tissue, comprising:
    an elongated cannula, having a distal and proximal ends; and
    a tapered tip, attached to the distal end of the elongated cannula, comprising:
    a pair of protrusions extending laterally from the tip, each protrusion positioned on opposite sides of the tip.

11. The apparatus of claim 10, wherein the pair of protrusions have distal ends disposed near the distal end of the tip.

12. The apparatus of claim 10, wherein the pair of protrusions are in a planar configuration and are tapered towards the distal end of the cannula.

13. The apparatus of claim 12, wherein the pair of protrusions are in a planar configuration and curved in a parabolic configuration.

14. A method of dissecting and transecting vessels using a cannula having a selectively displaceable tip disposed on the distal end of the cannula, the tip having an axis aligned with a central axis of an endoscopic lumen which is eccentric to a central axis of the cannula, comprising the steps of:
    incising skin to expose an area near a target vessel;
    bluntly dissecting the incision to expose the target vessel;
    sealing the incision;
    insufflating a tunnel along the target vessel;
    advancing the cannula through tissue along the target vessel under endoscopic visualization through the offset tip to form a tunnel in tissue adjacent the target vessel;
    removing the cannula from the tunnel;
    removing the offset tip from the distal end of the cannula;
    inserting the cannula into the tunnel through the incision; and
    transecting side branches and vessel ends under endoscopic visualization through use of endoscopic instruments in cannula.

15. The method of claim 14 performed using a transparent dilating tip having a pair of protrusions bilaterally extending therefrom, the method further comprising the steps of:
    substituting the dilating tip for the offset tip;
    advancing the cannula under endoscopic visualization through the dilating tip along the insufflated tunnel to dissect tissue surrounding the tunnel in response to advancement of the cannula and dilating tip therethrough;
    removing the cannula and dilating tip from the tunnel; and
    removing the dilating tip.

16. A method of dissecting and transecting vessels using a cannula having a selectively displaceable tip disposed on the distal end of the cannula, the tip having an axis aligned with a central axis of an endoscopic lumen which is eccentric to a central axis of the cannula, the method comprising the steps of:
    incising skin to expose an area near a target vessel;
    bluntly dissecting the incision to expose the target vessel;
    advancing the cannula through tissue along the target vessel under endoscopic visualization through the offset tip to form a tunnel in tissue adjacent the target vessel;
    removing the cannula from the tunnel;
    removing the offset tip from the distal end of the cannula;
    inserting the cannula into the tunnel through the incision; and
    transecting side branches and vessel ends under endoscopic visualization using endoscopic instruments extended through the cannula distally of the distal end thereof.

17. The method according to claim 16 including:
sealing the incision; and
insufflating a tunnel along the target vessel.

18. A method of dissecting and transecting vessels using a cannula having a selectively displaceable transparent tip disposed on the distal end of the cannula, comprising the steps of:
incising skin to expose an area near a target vessel;
bluntly dissecting the incision to expose the target vessel;
sealing the incision;
insufflating a tunnel along the target vessel; and
advancing the cannula through tissue along the target vessel under endoscopic visualization through the transparent tip to form a tunnel in tissue adjacent the target vessel;
removing the cannula from the tunnel;
removing the tip from the distal end of the cannula;
inserting the cannula into the tunnel through the incision; and
transecting side branches and vessel ends under endoscopic visualization through use of endoscopic instruments in the cannula.

* * * * *